US009211114B1

(12) United States Patent
Fromm et al.

(10) Patent No.: US 9,211,114 B1
(45) Date of Patent: Dec. 15, 2015

(54) METHOD OF COATING TISSUE TO PROMOTE SOFT TISSUE AND BONE TISSUE HEALING, INVOLVING NANOTECHNOLOGY, AND A PHOTONIC CURING SYSTEM FOR USE IN REPAIRING TISSUE

(75) Inventors: Stuart Fromm, Rapid City, SD (US); Dana Medlin, Omaha, NE (US)

(73) Assignee: FM-Nanocoat, LLC, Rapid City, SD (US)

( * ) Notice: Subject to any disclaimer, the term of this patent is extended or adjusted under 35 U.S.C. 154(b) by 714 days.

(21) Appl. No.: 13/353,986

(22) Filed: Jan. 19, 2012

Related U.S. Application Data

(60) Provisional application No. 61/443,057, filed on Feb. 15, 2011.

(51) Int. Cl.
*A61N 5/06* (2006.01)
*A61B 17/00* (2006.01)

(52) U.S. Cl.
CPC . *A61B 17/00491* (2013.01); *A61B 2017/00504* (2013.01)

(58) Field of Classification Search
CPC ............ A61B 17/00491; A61B 2017/005; A61B 17/12195; A61B 2017/00504; A61B 2017/00513
USPC ....................................... 128/898; 607/88–94
See application file for complete search history.

(56) References Cited

U.S. PATENT DOCUMENTS

| | | | |
|---|---|---|---|
| 4,595,713 A | 6/1986 | St. John | |
| 6,478,809 B1 * | 11/2002 | Brotz | 606/228 |
| 6,875,461 B2 | 4/2005 | Tanaka et al. | |
| 7,776,600 B2 | 8/2010 | Kumta et al. | |
| 8,160,678 B2 * | 4/2012 | Cropper et al. | 600/427 |
| 2007/0071790 A1 | 3/2007 | Ameer et al. | |
| 2007/0259427 A1 | 11/2007 | Storey et al. | |
| 2009/0317446 A1 * | 12/2009 | Tan et al. | 424/423 |

(Continued)

FOREIGN PATENT DOCUMENTS

WO 2008/028194 3/2008
WO 2008/070186 6/2008

(Continued)

OTHER PUBLICATIONS

Carter, et al., "Photonic Curing for Sintering of Nano-Particulate Material", Advances in Powder Metallurgy and Particulate Materials, 2007, No. 2, pp. 09-68-09-75.

(Continued)

*Primary Examiner* — Aaron Roane

(74) *Attorney, Agent, or Firm* — Caesar Rivise, PC

(57) ABSTRACT

A method for promoting soft tissue to soft tissue growth, soft tissue to bone tissue growth or bone tissue to bone tissue growth including coating the soft tissue or bone tissue with a nano-composition that encourages growth and photonically curing the composition to the soft tissue or bone tissue after it has been coated such that the soft tissue or bone tissue is not substantially damaged. A photonic curing system for use in repairing hard or soft tissue in a medical procedure is also provided includes a coating device for coating the tissue with a nano-composition that encourages growth, and a curing device for curing the composition to the tissue after it has been coated such that the first tissue is not substantially damaged.

11 Claims, 2 Drawing Sheets

(56) References Cited

U.S. PATENT DOCUMENTS

| | | |
|---|---|---|
| 2010/0040668 A1 | 2/2010 | Riman et al. |
| 2010/0047309 A1 | 2/2010 | Lu et al. |
| 2010/0136117 A1 | 6/2010 | De Groot |
| 2010/0178312 A1 | 7/2010 | Webster et al. |

FOREIGN PATENT DOCUMENTS

| | | |
|---|---|---|
| WO | 2008/089109 | 7/2008 |
| WO | 2008/100534 | 8/2008 |
| WO | 2010/062561 | 6/2010 |

OTHER PUBLICATIONS

Colvin, et al., "Fabrication of Conductors and Inductors by Nano-Particle Deposition Through Direct Write Technology", Journal of Microelectronics and Electronic Packaging, vol. 3, No. 3, pp. 121-128, 2006.

Carter, et al., "Sintering Nano-Particles on Low Temperature Materials", Paper # M1102, ICLAEO Conference Proceedings, 2006.

Novacentrix, Cost Considerations for Photovoltaics on Flexible Substrates, Jun. 2008.

Lu, et al., "Tissue Engineering Strategies for the Regeneration of Orthopedic Interfaces", Annals of Biomedical Engineering, vol. 38, No. 6, Jun. 2010.

\* cited by examiner

METHOD OF COATING TISSUE TO PROMOTE SOFT TISSUE AND BONE TISSUE HEALING, INVOLVING NANOTECHNOLOGY, AND A PHOTONIC CURING SYSTEM FOR USE IN REPAIRING TISSUE

CROSS-REFERENCE TO RELATED APPLICATION

This application claims priority to U.S. Provisional Application Ser. No. 61/443,057, entitled Soft Tissue Coatings to Promote Soft Tissue-To-Soft Tissue Healing, Involving Nanotechnology, filed Feb. 15, 2011.

BACKGROUND OF THE INVENTION

The present application is directed to a method of using hydroxyapatite or similar materials that promote tissue growth in tissue repair procedures.

Hydroxyapatite (HA) has been around for many years and is the most dependable source for enhancing the "activity" of bone. Hydroxyapatite is used for coating total joint/joint replacements to enhance bone growth into metal prosthetics ("bony ingrowth" prosthetics). In other words, the use of bony ingrowth prosthetics is very popular in the world of orthopedic surgery because the surgeon then does not have to cement or "glue" the pieces in. Porous metals for orthopedic applications have a mesh that allows bone to grow into the metal components. By coating the metal with hydroxyapatite, bone growth into the metal is encouraged. Hydroxyapatite makes such growth faster and more reliable. Hydroxyapatite is also used as a bone graft substitute—to enhance fracture healing, especially in hard to heal fractures such as tibia fractures.

It is known that nano-hydroxyapatite (nano-HA) is also affective for such applications. For purposes of the present invention, nano-HA is defined as HA particles less than 100 nanometers in size, both spherical and nonspherical. When HA is applied to metal components it is done via a high-temperature process sometimes called plasma spraying. This high-temperature process is not suitable for soft tissues because it will destroy the protein materials.

HA can be applied by dipping, but it needs to be partially or fully melted, so it will not be removed by water due to its solubility. HA can be placed on the surface of a soft tissue, hard tissue, metal, ceramic, polymer, but it will quickly be washed off the surface by water. The HA can be partially or fully melted on a substrate by thermally heating (oven or furnace), laser heating, electron beam, or other direct heat source, This direct applied heat will melt (consolidate) the HA and destroy the soft tissue substrates.

Healing of the body, other than healing of bone, occurs with growth of scar tissue/fibrous tissue. Any kind of tendon repair, ligament reconstruction, vascular implant, etc. will heal with scar tissue. Fibrous tissue/scar tissue is usually not as strong as the native tissue, and therefore re-injury is a risk. That is, unlike a bone fracture that will typically appear completely normal after it heals, soft tissue that heals will always look abnormal. If a bone fracture does not unite ("non-union"), it will heal with what is called a "fibrous union"— literally the fracture will bridge with scar tissue. The problem is that the fracture remains unstable and painful and the fibrous union must typically be removed to enable bony union healing.

Another downside of healing with fibrous tissue is that it can stretch out as it heals. Bone does not do this. If healing time can be reduced from, for example, six months to six weeks, such stretching can be minimized such that long-term failure is far less likely. Patients may return much more quickly to work, sports, and other normal daily activity.

Known patent documents in the general field include the following:

U.S. Pat. No. 7,776,600 (Kumta et al.) (U.S. Publication No. 20089/0095820) is directed to a method for production of nanocrystalline HA for use in prosthetic tooth engineering and repair. As discussed at paragraph 0081 and 0082, this HA is used for cartilage tissue engineering and ligament repair by direct injection.

U.S. Pat. No. 6,875,461 (Tanaka et al.) is directed to a method for coating a calcium phosphate compound on a bio tissue substrate where the method causes no damage, using a soaking method. This invention is used in the repairing soft tissue to bone.

U.S. Pat. No. 4,595,713 (St. John) is directed to a medical implant for regeneration of soft and hard connective tissue. Chopped carbon fiber is used in a mass of a copolymer that is molded to the void to be filled or in the shape of the tissue desired and implanted in the patient. The mass is gradually replaced by regenerated tissue.

U.S. Patent App. Publication No. 2010/0178312 (Webster et al.) is directed to compositions and methods for enhancing attachment of soft tissues to metal prosthetic devices. The metal has a nano-textured surface.

U.S. Patent App. Publication No. 2010/0136117 (De Groot) is directed to an HA tissue filler composition suitable for use in soft tissue repair which includes ceramic particles less than 15 or 20 μm. The composition may be in a form that is injectable. Use for reducing recovery time is not discussed.

U.S. Patent App. Publication No. 2010/040668 (Riman et al.) is directed to methods for preparing composite materials which include nanoscale HA. One of the goals is for HA synthesis to take place at room temperature and optional neutral pH to allow the exploration of synthesis with live cells, including those in living organisms. This publication does not explicitly teach use on soft tissue, such as tendons and ligaments.

U.S. Patent App. Publication No. 2010/0047309 (Lu et al.) discloses methods and apparatus for tissue engineering in the form of graft collars and scaffolds. The graft collars comprise a mesh for fixing tendon to bone. Examples are given of ACL grafts.

U.S. Patent App. Publication No. 2009/0317446 (Tan) discloses calcium phosphate nanofiber matrices used to culture bone and dental cells and as implants to treat bone, dental or periodontal diseases and defects.

U.S. Patent App. Publication No. 2007/0071790 (Ameer et al.) is directed to a nano-composite used in soft tissue engineering, such as cartilage, ligaments and tendons.

U.S. Patent App. Publication No. 2007/0258427 (Storey et al.) discloses nano-particle deposition on selected substrates to enhance tissue attachment.

International Publication No. WO/062561 (PCT/US2009/062077) (University of Arkansas) is directed to methods, compositions, etc. in which a material such as HA is combined with a nano-particle composition to form a material delivered to a cell or tissue (including soft tissues). The material may be a coating for an implant.

International Publication No. WO 2008/028194 (PCT/US2007/077560) (Cornell Research Foundation, Inc.) is directed to calcium phosphate nano-fiber matrices used to culture bone and dental cells and as implants to treat bone, repair of body parts, skin grafts, etc.

International Publication No. WO 2008/089109 (PCT/US2008/050940) (Rutgers University) discloses methods for preparing composite materials which include nanoscale HA. At page 5, it is noted that, in the past, HA reaction conditions used high temperatures, high pressures, and extreme pH values such that biological applications are limited.

International Publication No. WO 2008/100534 (PCT/US2008/0018889) (Columbia University) is directed to a nanofiber scaffold for soft tissue and soft tissue-to-bone repair. HA may be incorporated into the scaffold.

International Publication No. WO 2008/070186 (PCT/US2007/025127) (Columbia University) is directed to a scaffold for promoting tendon-to-bone fixation. (similar to Lu application above).

All references cited herein are incorporated herein by reference in their entireties.

BRIEF SUMMARY OF THE INVENTION

In a first exemplary embodiment of the present invention, a method for promoting growth of a first soft tissue to bone or promoting growth of a first soft tissue to a second soft tissue growth is provided. The method includes the steps of coating the first soft tissue with a nano-composition that encourages growth, and photonically curing the composition to the first soft tissue after it has been coated such that the first soft tissue is not substantially damaged.

The composition that encourages growth is preferably nano-hydroxyapatite, but may be other nano-compositions. The step of photonically curing may utilize a xenon or other type of flash lamp and may be integral to an arthroscope. The first soft tissue may be, for example, ACL grafts, cartilage, ligaments, tendons, and the like. Preferably, the nano-composition has a particle size of less than about 100 nanometers. Preferably, the size distribution of the nano-composition is consistent. The nano-composition may be in a solution that is biocompatible with human tissue and which is sprayed on the first soft tissue, Here, the solution evaporates to leave a dry thin coating of the nano-composition on the first soft tissue. The nano-composition may be in a solution that is biocompatible with human tissue, wherein the first soft tissue is dipped into the nano-composition. Again, here, the solution evaporates to leave a dry thin coating of the nano-composition on the first soft tissue. The nano-composition may be in a solution in a range from less than 5% to over 70% nano-hydroxyapatite in ethanol, and preferably about is about 30% nano-hydroxyapatite in ethanol. The particle size of the nano-composition may have a mean particle size of about 20-30 nanometers. The nano-composition may be sprayed on using, for example, a programmed three dimensional coordinate spray system, sometimes called Direct Write. The nano-composition may be in a solution sprayed on using a plurality of passes that yield coatings of nano-composition that are approximately 0.1 to 5.0 μm thick, with each layer being substantially dry before a subsequent layer is sprayed. The layer may or may not be photonically cured after drying depending upon the total coating thickness. Once the coating is thicker than 5 μm, the penetration of the photonic curing is limited.

In a second exemplary embodiment of the present invention, a method for promoting growth of a first bone tissue to a second bone tissue or growth of a first bone tissue to a soft tissue is provided. The method includes the steps of coating the first bone tissue with a nano-composition that encourages growth, and photonically curing the composition to the first bone tissue after it has been coated such that the first bone tissue is not substantially damaged.

The composition that encourages growth may be nano-hydroxyapatite. The step of photonically curing may utilize a xenon flash lamp. The nano-composition may be a particle size of less than about 100 nanometers. The size distribution of the nano-composition is preferably consistent. The nano-composition may be in a solution that is biocompatible with human tissue and is sprayed on the first bone tissue, wherein the solution evaporates to leave a dry thin coating of the nano-composition on the first bone tissue. The nano-composition may be in a solution that is biocompatible with human tissue, wherein the first bone tissue is dipped into the nano-composition, wherein the solution evaporates to leave a dry thin coating of the nano-composition on the first bone tissue. The nano-composition may be in a solution in a range from less than 5% to over 70% nano-hydroxyapatite in ethanol. The nano-composition may be in a solution in about 30% nano-hydroxyapatite in ethanol. The particle size of the nano-composition may have a mean particle size of about 20-30 nanometers or less. The nano-composition may be sprayed on using a programmed 3-D coordinate spray system. The nano-composition may be in a solution sprayed on using a plurality of passes that yield coatings of nano-composition that are approximately 0.1 to 5.0 μm thick, with each layer being substantially dry before a subsequent layer is sprayed and photonically cured. The first bone tissue may be allograft bone (for example, in the form of "croutons" as known to those skilled in the art, but also any other size and configuration, including small chips, large "strut grafts, cortical and cancellous bone).

In a third exemplary embodiment of the present invention, a photonic curing system is provided for use in repairing a first hard or a first soft tissue to a second hard or second soft tissue in a medical procedure. The system includes a coating device for coating the first tissue with a nano-composition that encourages growth, and a curing device for curing the composition to the first tissue after it has been coated such that the first tissue is not substantially damaged.

The nano-composition may be nano-hydroxyapatite. The particles of the nano-composition are preferably less than 100 nanometers. The curing device may be a xenon flash lamp that emits at least one brief, intense pulse of light. The coating device may be a sprayer for spraying the nano-composition that is suspended in a solution. The sprayer may be programmable in a 3-D coordinate system.

Bone-to-bone healing typically takes about six weeks to heal, yet any kind of soft tissue healing to this point, including soft tissue to bone tissue (i.e., hard tissue) such as a ligament repair, or soft tissue to bone tissue such as a rotator cuff repair, typically takes six months to heal. The present invention enables "tricking" the body into thinking it was healing with bone tissue rather than scar tissue.

Benefits of the present invention include the following: Surgeries may be more successful because the type of tissue healing is much more successful (bone-to-bone type healing on soft tissue rather than soft tissue-to-bone tissue or soft tissue-to-soft tissue type healing). Additionally, the window of healing may be dramatically shortened which dramatically shortens the time that failure can occur (for many reasons—the soft tissue can re-tear, stretch, or develop an area of weakness). Also, by shortening the healing rate—the patient can return to their sport, work, etc. much more quickly In some embodiments of the present invention, these goals are accomplished by coating soft tissues with a material that tricks the body into thinking it is healing via bone and not via scar tissue/fibrous tissue. This is accomplished by coating the soft tissues with HA (or similar known material) since HA is currently the most accepted way to encourage bone to heal via bone. The mainstay of this is by coating total joint prosthetics (either by HA mesh, coatings, or plasma spray, etc.). Coating allograft tissue (dead cadaver tissue) would simply destroy the tissue due to traditional thermal application techniques. The present invention coats soft tissues with nanometer size HA at room temperatures—conditions that would not change the soft tissue at all. With nanotechnology of the present invention, soft tissues are thermally treated (cured) with a flash of light. A tendon, living tissue, for example, in the shoulder may be coated with nano-HA and then cured with a flash of light from, for example, an arthroscope. This can also be done outside the body with free standing or bench-top photonic curing systems.

BRIEF DESCRIPTION OF SEVERAL VIEWS OF THE DRAWINGS

The invention will be described in conjunction with the following drawing and wherein.

DETAILED DESCRIPTION OF THE INVENTION

Figure 1:
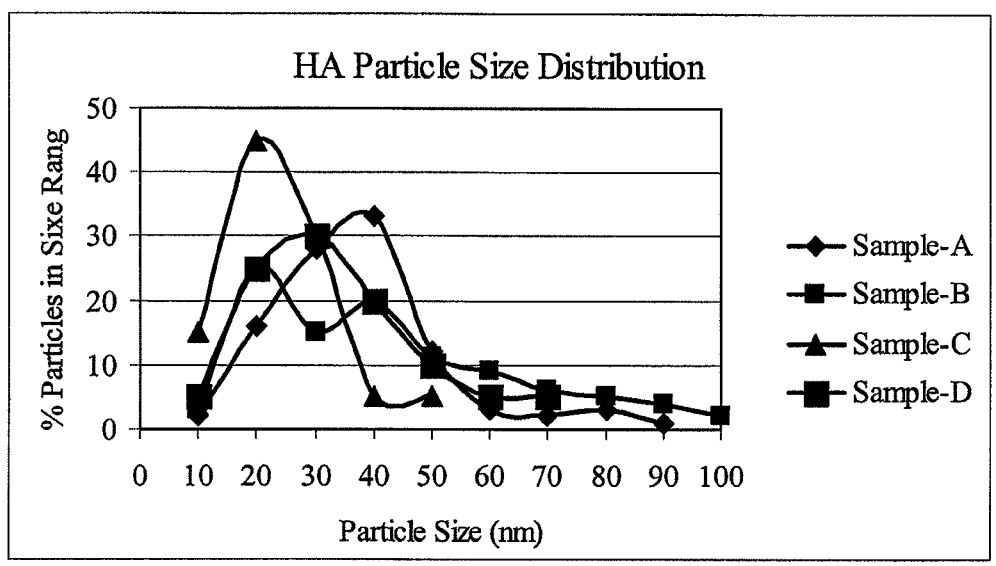
FIG. 1 is a graph of HA particle size distribution for four different nano-HA solution samples.

The present invention is directed to applying coatings that promote healing of tissue such as hydroxyapatite (HA) on a nanoscale to soft tissue such as tendons and ligaments and/or to hard tissue such as bone tissue to speed up healing. Prior uses of HA and similar coatings to soft tissues typically required application of heat at temperatures that injure or destroy soft tissues. The use of nanotechnology allows for substances such as HA to be applied at generally body or room temperature. The present invention uses a flash of light, from, for example, an arthroscope, in the curing process. The use of nanotechnology in combination with the flash of light allows for HA or similar growth encouraging compositions to be applied at generally body or room temperature.

The present invention is directed to coating soft tissues such as ligaments and tendons with hydroxyapatite to enhance their healing, as well as coating hard tissues, such as bone tissues, to enhance their healing. For example, a surgery that typically takes four to six months to heal may take only four to six weeks to heal using the method and system of the present invention. Coating a tissues such as a ligament by prior methods does not work in that heat destroys the tissue and kills viable cells (if using living tissue). Through nanotechnology, soft tissues, bone tissues and other living tissues, can be coated with nano-hydroxyapatite and then cured using a flash of a light at ambient room temperatures. This invention has numerous applications and can be used for all specialties of surgery—and may be used be on living tissue within a patient (such as a rotator cuff repair in a patient's shoulder for orthopedic surgery).

The present invention is directed to the use of photonic curing to consolidate nano-particles of hydroxyapatite onto tissues (e.g., ACL grafts, rotator cuff repairs, etc.) for improved soft tissue-to-soft tissue, or soft tissue-to-bone tissue, or bone tissue to bone tissue healing. The photonic curing process consolidates nano-particle materials at temperatures near 100° C. without heating the substrate tissues, or with minimal substrate heating. In addition, materials or tissues that are not coated with hydroxyapatite can be masked and not heated above ambient temperature during the curing process. This invention is directed to significant improvements in tissue-to-tissue healing for repair or reconstructive surgeries.

Advances in the development of metallic and ceramic nano-particles (less than 100 nanometers) have resulted in numerous physical and mechanical property changes when these same materials are compare to conventional particles sizes (>500 nanometers). One of significant discoveries of nano-particle research was that the melting point of metallic and ceramic materials decreases as the particle size decreases. For example, gold (Au) normally has a melting point of approximately 1063° C. However, when the particle size of the gold is reduced to less than 20 nanometers, the melting point decreases to less than 300° C. Similar decreases in the melting point have been evaluated with silver, nickel, zirconium oxide, barium-titanium oxide, cobalt alloys, mica, etc. Sintering (i.e., melting) of the nano-particles has traditionally been accomplished by thermal activation processes such as conventional furnace heating and low-temperature laser melting. However, this has limited the development of consolidating nano-particles onto low temperature substrates such as plastics and soft tissues due to the thermal breakdown of the substrate materials at these temperatures.

Photonic curing is a technique that melts (consolidates) metallic and ceramic (including HA) nano-particles together by exposing them to a brief, intense pulse of light from a flash lamp, such as a xenon flash lamp. A single or multiple pulses of light can be used for curing. This technology allows for rapid and selective heating that fuses (partially or fully melts) nanoscale particles into thin adhering layers onto low-temperature substrates. To date, this technology has been evaluated to develop basic electrical components such as capacitors, inductors and resistors onto low-temperature substrates such as Kapton®, Mylar® and polyethylene. Not only does this process limit the amount of heat that the substrate material encounters, but areas that do not need to be exposed to heat can be masked from the light source and not receive any heat input.

The present invention is directed to coating nano-particle HA onto the ends of soft and hard tissues, and photonically curing (consolidating) the HA without heating the substrate tissues. The consolidated HA on the ends of the grafts would decrease the healing time for soft tissue reconstruction repairs by making the soft tissue grafts heal more like a bone-tendon-bone reconstructions.

In order for nano-particles of HA to consolidate via photonic curing, they must be below 100 nanometers in size. Particles smaller than 50 nanometers will typically react better to the photonic curing. Essentially, the smaller the particles are in size, the better the particles respond to the photonic curing process. Another important issue is the consistency of the nano-particle powder. It is critical that the size distribution be particles be as narrow as possible. A mixture of small particles with some percentage of larger particles will impede the photonic curing process.

The nano-particle HA must be suspended in a solution so the HA particles can be placed on the surface by either dipping the substrate into the solution or by spraying the solution onto the surface. In addition, the liquid must be able to evaporate quickly and leave a dry thin coating of nano-HA on the surface. It is critical for the liquid to quickly vaporize and thoroughly dry after application (dipping or spraying) because any residual liquid remaining in the applied nano HA may interfere with the photonic curing process. These particles can be suspended in a variety of liquids; however, the liquid must be biocompatible with human tissues and have minimal adverse reactions to the human body. One such liquid that has appropriate characteristics for use with the present invention is ethanol.

A nano-particle HA material appropriate for the present invention may be obtained from, for example, Fluidinova (of Portugal), Berkley Advanced Biomaterials (of Berkeley Calif.), and other companies. Suitable solutions can be obtained from the manufacturers in concentrations ranging from <5% to over 70% nano-HA in ethanol.

Testing was performed initially using a 30% concentration of nano-HA in ethanol and was evaluated with a scanning electron microscope and a submicron particle analyzer to determine the particle size, shape, aspect ratio and distribution. Understanding the particle size, shape and distribution are critical when determining the proper phonic curing parameters for optimum consolidation. Excessive melting will cause liquid HA flow and solidification cracking during the processing which is not desired. The optimal process parameters will result in a consolidated (partially melted) HA layer with some remaining nano-texturing for the most advantageous osteoconduction.

An important particle size characteristic is particle size distribution. A wide particle size distribution will result in both high and low melting point particles and make the photonic cure processing more complicated, if not incomplete. A reliable and narrow distribution will make the photonic cure process more consistent and controllable.

Analysis has shown that there is a large variance in the distribution depending upon the manufacturer. See FIG. 1. Four samples were analyzed, samples A, B, C and D. The particle size distribution of sample-A was the smallest and the mean particle size was approximately 20 nanometers which is substantially smaller than the mean distributions of the other samples. The smaller the distribution and the smaller the mean particle size, the superior the photonic curing process will be. Based on these data, a 30% ethanol solution of nano HA was used from Sample-A.

The photonic curing process has several process parameters including applied voltage, applied current, distance between sample and flash lamp, light absorption efficiency, material thickness, and time of exposure. One suitable photonic curing system is the PCS-1100 manufactured by Novacentrix of Austin, Tex.

A direct write spray system by, for example, the M3D by Optomec of Albuquerque, N. Mex. may be used to spray the thin layers of nano-HA solution onto the substrate. The spray nozzle is capable of being programmed with a 3-D coordinate system for accurate spray width and speed. The speed of the nozzle determines the coating thickness. Other direct write systems may be used that may vary the thickness, for example, by changing the nozzle pressure. In order to minimize the number of variables in the spray process, the thinnest layer of HA was sprayed onto the substrate and then multiple spray passes were made. It was estimated that a single spray pass applied approximately 0.1 µm thick layer of nano HA onto the surface. The layer was allowed to air dry for several minutes while the ethanol dried before another layer was applied. The dried layer can be photonically cured between each spray pass to consolidate the nano-HA.

A series of tests were conducted to optimize the HA coating thickness and phonic cure processing variables. An initial set of experiments involved coating multiple layers of HA at various thicknesses and then photonically curing the layers at a standard set of lamp voltages, currents and exposure times. Table-1 shows the initial set of photonic cure parameters used in this analysis and this was expanded during additional testing.

TABLE 1

Initial Photonic Cure Parameters

| Lamp Voltage (V) | Lamp Time (µs) |
|---|---|
| 1200 | 600 |
| 1200 | 800 |
| 1200 | 900 |
| 1200 | 1000 |
| 1200 | 1200 |
| 1400 | 600 |
| 1400 | 800 |
| 1400 | 1000 |
| 1400 | 1200 |
| 1400 | 1400 |
| 1600 | 600 |
| 1600 | 800 |
| 1600 | 1000 |
| 1600 | 1200 |
| 1600 | 1400 |

Each set of experiments was evaluated by light microscopy and scanning electron microscopy to determine the level of particle consolidation. Small changes (iterations) in the HA ethanol solution concentration, HA layer thickness, and photonic cure process variables were adjusted and evaluated to optimize the final HA consolidated layer thickness and surface texture. The goal of this laboratory work was to develop a fully consolidated HA layer with some remaining nano-scale surface texture for improve osteoconduction with bone tissue. Once completed, the test was repeated to validate the process parameters.

It is important to determine the amount of heat transfer (flux) occurring at the interface between the consolidated HA layer and the substrate material. Significant heating of the HA and conduction of this heat into the substrate may cause excessive damage to the underlying soft tissues and possibly affect soft tissue to bone adhesion. The amount of heat transfer from the photonically cured HA into the substrate material can be estimated by curing the HA onto low-temperature melting polymers and analyzing the interface layer between the HA and the substrate for excessive heat damage and deformation. Table-2 lists some of the low-temperature polymers that have been used to evaluate the interface layer in the past, so these will be used to determine the heat transfer with consolidated nano HA. The basic idea of this test is to spray a thin layer (<0.10 µm) of nano HA onto each of these substrates and then photonically cure the samples. If substantial heat transfer takes place between the consolidated HA and the underlying polymer, the polymer will melt and based on the melting point of the polymer we can estimate the amount of heat at the interface. Kapton has a melting temperature of 450° C. and the polymer weave is less than 75° C. with the other polymers having a melting point somewhere between these two extremes.

TABLE 2

Low-Temperature Polymers Used to Evaluate Interface Heat Damage

| LOW-TEMPERATURE POLYMER | MELTING TEMPERATURE (° C.) |
|---|---|
| Kapton | 450 |
| Transparency Sheet | 135 |
| Mylar | 105 |
| LM Material | 82 |
| Low Temperature Mylar | 78 |
| Polymer Weave Material | <75 (variable) |

The results showed that the polymer weave and the low temperature Mylar substrates had indications of melting and that the LM material was inconclusive. The LM material may have had small areas of melting; however, it was not as clear as the two other polymers. The other samples did not show any indications of substrate melting. It was concluded that with a coating thickness of 0.1 micrometers the interface between the nano HA and the substrate reached a temperature no higher than 90° C.

The final experiment was to coat 10 grafts (tendons) and evaluate the integrity of the grafts for homogeneity and depth of the HA (calcium) penetration into the graft using light microscopy and scanning electron microscopy. Ten grafts were coated with the processing variables determined in the previous research steps. The graft samples were evaluated for additional analysis including HA and graft interface integrity in cross section. Two samples of each nano HA thickness were made according to Table-3.

TABLE 3

Nano HA Coating Thickness on Grafts (Tendons).

| SAMPLE ID | HA THICKNESS micro-meters (μm) | HA (CALCIUM) PENETRATION (μm) |
|---|---|---|
| Sample 1 | 0.2 | 70-80 |
| Sample 2 | 0.4 | 50-55 |
| Sample 3 | 0.6 | 20-30 |
| Sample 4 | 0.5 | NA |
| Sample 5 | 2.0 | 55-90 |

The results of the analysis revealed that samples 1-3 were considered "good" and samples 4-5 were "not as good". Basically, the thinner coats of nano-HA resulted in deeper HA (calcium) penetration into the graft which translates back to the amount of optimum photonic curing consolidation that occurred due to HA coating thickness. A thinner HA coating will likely develop better consolidation. A thick layer of HA will not receive as much light penetration into the deeper layers and, therefore, the deeper layers will not consolidate properly. Nano HA layers less than 0.5 μm were found to be optimum for this processing technique.

Figure 2:
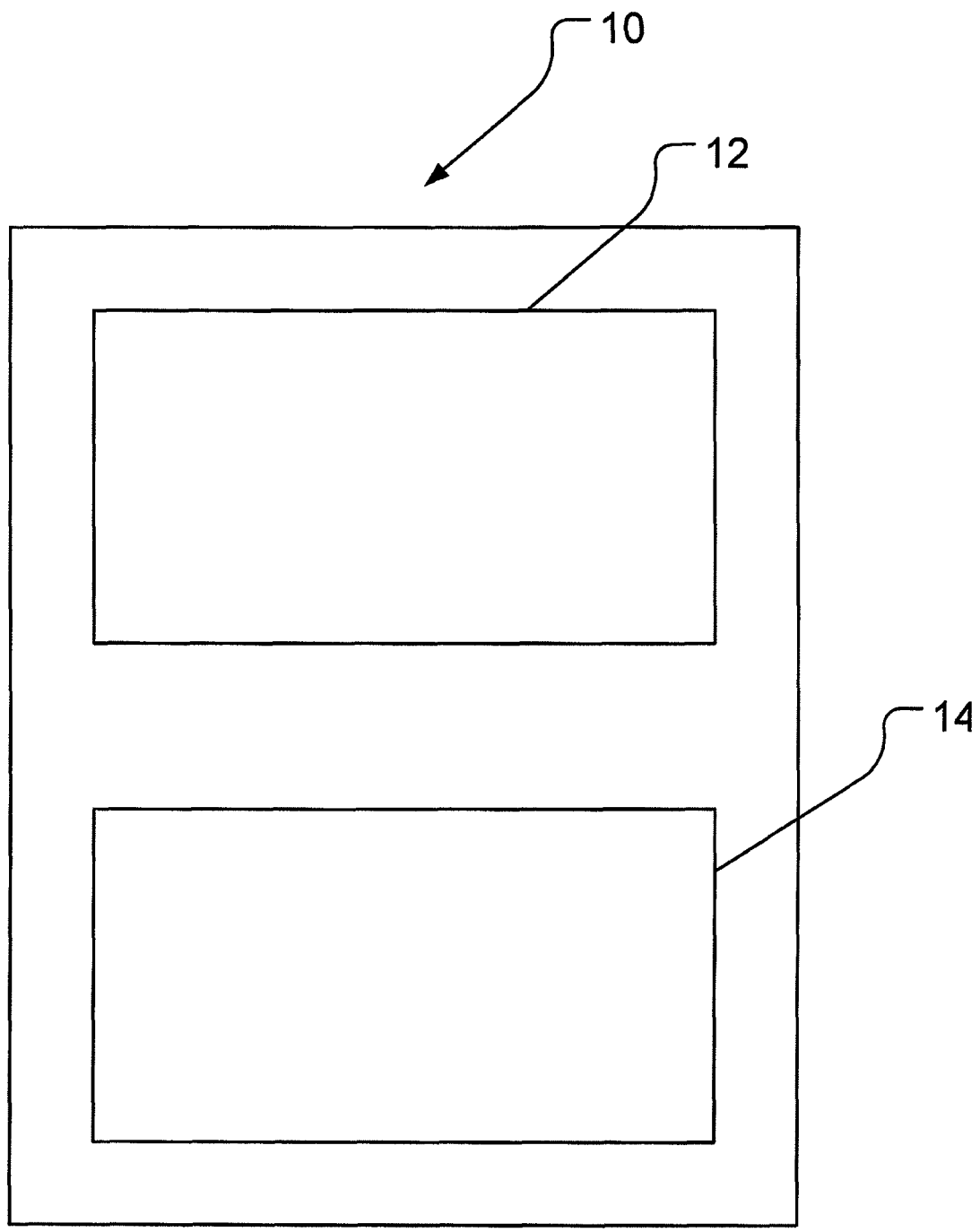
FIG. 2 is a system photonic curing system for use in repairing hard or soft tissue in accordance with a first exemplary embodiment of the present invention.

As can be seen in FIG. 2, a photonic curing system 10 for use in repairing a first hard or soft tissue to a second hard or soft tissue in medical procedure is also provided. The system 10 includes a coating device 12 for coating the first tissue with a nano-composition that encourages growth; and a curing device 14 for curing the composition to the first tissue after it has been coated such that the first tissue is not substantially damaged. The curing system 10, can be incorporated into a standard medical device such as an arthroscope.

Finally, it is the intent of the present invention, when discussing soft tissue and bone tissue, to include any type of live or cadaveric tissue.

While the invention has been described in detail and with reference to specific examples thereof, it will be apparent to one skilled in the art that various changes and modifications can be made therein without departing from the spirit and scope thereof.

What is claimed is:

1. A method for promoting a first soft tissue to bone growth or promoting a first soft tissue to second soft tissue growth in a body of a being, comprising:
   (a) coating the first soft tissue with nanohydroxyapatite wherein the coating occurs outside of the body; and
   (b) photonically curing the composition to the first soft tissue after it has been coated such that the first soft tissue is not damaged, wherein the curing occurs outside of the body.

2. The method of claim 1, wherein the step of photonically curing utilizes a xenon flash lamp.

3. The method of claim 1, wherein the nano-composition is in a solution in a range from less than 5% to over 70% nano-hydroxyapatite in ethanol.

4. The method of claim 1, wherein the nano-composition is in a solution in 30% nano-hydroxyapatite in ethanol.

5. A method for promoting a first soft tissue to bone growth or promoting a first soft tissue to second soft tissue growth in a body of a being, comprising:
   (a) coating the first soft tissue with a nano-composition having a particle size of less than 100 nanometers that encourages growth, wherein the coating occurs outside of the body; and
   (b) photonically curing the composition to the first soft tissue after it has been coated such that the first soft tissue is not damaged, wherein the curing occurs outside of the body.

6. The method of claim 5, wherein the particle size of the nano-composition has a mean particle size of 20-30 nanometers or less.

7. A method for promoting a first soft tissue to bone growth or promoting a first soft tissue to second soft tissue growth in a body of a being, comprising:
   (a) coating the first soft tissue with a nano-composition that encourages growth, wherein the coating occurs outside of the body, wherein the size distribution of the nano-composition is consistent; and
   (b) photonically curing the composition to the first soft tissue after it has been coated such that the first soft tissue is not damaged, wherein the curing occurs outside of the body.

8. The method of claim 7, wherein the nano-composition is in a solution that is biocompatible with human tissue and is sprayed on the first soft tissue, wherein the solution evaporates to leave a dry thin coating of the nano-composition on the first soft tissue.

9. The method of claim 7, wherein the nano-composition is in a solution that is biocompatible with human tissue, wherein the first soft tissue is dipped into the nano-composition, wherein the solution evaporates to leave a dry thin coating of the nano-composition on the first soft tissue.

10. The method of claim 7, wherein the nano-composition is sprayed on using a programmed 3-D coordinate spray system.

11. A method for promoting a first soft tissue to bone growth or promoting a first soft tissue to second soft tissue growth in a body of a being, comprising:
   (a) coating the first soft tissue with a nano-composition that encourages growth, wherein the coating occurs outside of the body; and
   (b) photonically curing the composition to the first soft tissue after it has been coated such that the first soft tissue is not damaged, wherein the curing occurs outside of the body
   (c) wherein the nano-composition is in a solution sprayed on using a plurality of passes that yield coatings of nano-composition that are approximately 0.1 to 5.0 μm thick, with each layer being dry before a subsequent layer is sprayed and photonically cured.

* * * * *